United States Patent
Zhou et al.

(10) Patent No.: US 9,254,349 B2
(45) Date of Patent: Feb. 9, 2016

(54) ENHANCING BIOCOMPATIBILITY OF A MEDICAL DEVICE

(75) Inventors: Zhengrong Zhou, St. Paul, MN (US); Stephanie M. Board, West St. Paul, MN (US); Anna Norlin-Weissenrieder, Stockholm (SE); Biyun Wu, Ann Arbor, MI (US)

(73) Assignee: St. Jude Medical, Inc., St. Paul, MN (US)

(*) Notice: Subject to any disclaimer, the term of this patent is extended or adjusted under 35 U.S.C. 154(b) by 102 days.

(21) Appl. No.: 13/147,236

(22) PCT Filed: Feb. 9, 2010

(86) PCT No.: PCT/US2010/000358
§ 371 (c)(1),
(2), (4) Date: Jan. 13, 2012

(87) PCT Pub. No.: WO2010/090767
PCT Pub. Date: Aug. 12, 2010

(65) Prior Publication Data
US 2012/0121657 A1    May 17, 2012

Related U.S. Application Data

(60) Provisional application No. 61/207,263, filed on Feb. 9, 2009.

(51) Int. Cl.
*A61L 27/30* (2006.01)
*A61L 31/08* (2006.01)

(52) U.S. Cl.
CPC .............. *A61L 27/303* (2013.01); *A61L 27/306* (2013.01); *A61L 31/084* (2013.01); *A61L 31/088* (2013.01)

(58) Field of Classification Search
None
See application file for complete search history.

(56) References Cited

U.S. PATENT DOCUMENTS

| | | | |
|---|---|---|---|
| 3,579,645 A | 5/1971 | Bokros | |
| 3,685,059 A | 8/1972 | Bokros et al. | |
| 3,969,130 A | 7/1976 | Bokros | |
| 7,128,904 B2 | 10/2006 | Batchelor et al. | |
| 7,604,663 B1 | 10/2009 | Reimink et al. | |
| 7,632,309 B1 | 12/2009 | Brendzel et al. | |
| 2003/0203991 A1* | 10/2003 | Schottman et al. | 523/334 |
| 2006/0039950 A1 | 2/2006 | Zhou et al. | |
| 2007/0014829 A1 | 1/2007 | Batchelor et al. | |
| 2007/0298354 A1* | 12/2007 | Ding et al. | 430/320 |
| 2009/0287072 A1* | 11/2009 | Meyerhoff et al. | 600/345 |

FOREIGN PATENT DOCUMENTS

| | | |
|---|---|---|
| EP | 0055406 | 7/1982 |
| JP | 49111912 | 10/1974 |
| JP | 57170811 | 10/1982 |
| JP | 2005500866 A | 1/2005 |
| JP | 4503050 B2 | 7/2010 |
| JP | 5058613 B2 | 10/2012 |
| WO | 0141826 A1 | 6/2001 |
| WO | 2007/064895 A2 | 6/2007 |

OTHER PUBLICATIONS

International Search Report and Written Opinion, PCT/US2010/000358, dated Jan. 5, 2011.
Yang et al., Langmuir 2008, 24, 10265-10272.
Hwang et al., Biomaterials 2008, 29, 2443-2452.
Lackey, Carbon 34(10):1299-1300 (1996).
Cha et al., "S-Notrosothiol Detection via Amperometric Nitric Oxide Sensor with Surface Modified Hydrogel Layer Containing Immobilized Organoselenium Catalyst", Langmuir, 2006, vol. 22, No. 25, p. 10830-10836.

* cited by examiner

*Primary Examiner* — Sue Liu
*Assistant Examiner* — Thor Nielsen
(74) *Attorney, Agent, or Firm* — Lerner, David, Littenberg, Krumholz & Mentlik, LLP

(57) ABSTRACT

The present invention relates to a medical device comprising both pyrolytic carbon and an NO generator, methods of making same, and methods of using same.

14 Claims, 1 Drawing Sheet

ENHANCING BIOCOMPATIBILITY OF A MEDICAL DEVICE

CROSS-REFERENCE TO RELATED APPLICATIONS

This application is a national phase entry under 35 U.S.C. §371 of International Application No. PCT/US2010/000358, filed Feb. 9, 2010, published in English, which claims the benefit of the filing date of U.S. Provisional Patent Application No. 61/207,263, filed Feb. 9, 2009, the disclosure of which is hereby incorporated herein by reference.

The present invention relates to a medical device comprising both pyrolytic carbon and an NO generator, methods of making same, and methods of using same.

BACKGROUND OF THE INVENTION

A variety of medical devices have been designed for use within a patient's body. Many such devices are surgically implanted and remain in the body for extended periods. Not surprisingly, the biocompatibility of the material used in these devices is a significant issue. The literature contains examples of methods and compositions designed to improve the biocompatibility, and particularly the hemocompatibility, of medical devices. These include attempts to reduce the formation of thromboses by modifying a surface of the device so that it contains anti-thrombotic agents. In addition, medical devices comprising ultra-smooth pyrolytic carbon, which is typically more biocompatible than devices made of inorganic materials or ceramics, is familiar to those of skill in the art and are described, for example, in U.S. Pat. No. 7,632,309.

While medical devices, and particularly cardiovascular prostheses, generally provide important clinical benefits, patients receiving these devices, including those devices comprised of pyrolytic carbon, typically must receive long term anticoagulant therapy. Such anticoagulant therapy may cause inconvenience to patients and adversely affect the quality of their lives. This is especially true for those who are in developing countries, where coagulation monitoring is not a standard care that is available in most of the clinics or hospitals. The cost of medication can also be an issue. Moreover, systemic administration of anticoagulants can produce hemorrhagic complications in patients at high risk of bleeding, including intracranial hemorrhage. Thus, alternative means for decreasing the risk of thromboses after post-surgical implantation of medical devices is desired.

Medical devices incorporating means to increase levels of nitric oxide (NO) in vivo after surgical implantation are also known. These are thought to work by increasing the thromboresistance of the device. See, for example, U.S. Pat. No. 7,128,904; U.S. Patent Application Publication No. 2007/0014829; U.S. Patent Application Publication No. 20090287072; Yang et al., *Langmuir* 2008, 24, 10265-10272; and Hwang and Meyerhoff, *Biomaterials* 2008, 29, 2443-2452. NO is a naturally occurring species that is generated by the endothelial cell (EC) layer that lines all blood vessels, and greatly contributes to the natural thromboresistance of the inner wall of healthy blood vessels. On the EC layer and/or (in some cases) within the blood, naturally occurring copper- and/or selenium-containing membrane proteins serve as catalysts to convert endogenous NO precursors (i.e., nitrosothial species (RSNO)) into the potent antiplatelet-agent NO. The nitrosothials are reported to be present in blood and other physiological fluids, where they are regenerated by the body via biological reactions, thereby maintaining their physiological basal levels.

U.S. Patent Application Publication No. 2009/0287072 specifically describes biocompatible, thrombo-resistant coatings for medical devices comprising the use of chalcogenide compounds as NO generators. There currently remains, however, a need for additional means to achieve an increase in biocompatibility, and particularly hemocompatability, of surgically implantable medical devices.

BRIEF SUMMARY OF THE INVENTION

In a first aspect, the invention relates to a medical device comprising both pyrolytic carbon or graphite and an NO generator. The device itself may be made of pyrolytic carbon or graphite. In these instances, the NO generator may be added directly during fabrication of the device, or may be deposited, plated or coated onto at least a portion of the device after the device has been formed.

In another aspect, the device is not itself made of, or made with pyrolytic carbon. The substrate can be made with, for example, graphite, metal or ceramic. In that instance, a biocompatible coating may be deposited, coated or otherwise applied to one or more surfaces of the medical device. In this instance, the device, or that part to which the biocompatible coating is applied, acts as a substrate. The biocompatible coating comprises pyrolytic carbon and an NO generator.

In some aspects, the devices of the present invention exhibit improved biocompatibility relative to devices made or coated with pyrolytic carbon. Yet the devices of the present invention remain nontoxic and retain an advantageous durability as well as other desirable physical properties. In other aspects, the invention provides medical devices with improved biocompatibility as well as providing other advantages such as local or systemic delivery of useful active agents.

In a particular embodiment, the biocompatible coating comprises at least one layer which comprises both the pyrolytic carbon and the NO generator in combination. This can be a homogeneous mixture or a heterogeneous mixture. The NO generator may be codeposited with pyrolytic carbon to form a biocompatible layer. Alternatively, the NO generator may be added to or deposited on a pyrolytic carbon layer or a pyrolytic carbon surface of a device made of pyrolytic carbon to form a biocompatible coating.

In another embodiment, the biocompatible coating further comprises one or more polymers. The biocompatible coating may comprise, for example, at least one layer comprising pyrolytic carbon, and a first polymer layer comprising at least one polymer and the NO generator. This polymer, and indeed any polymer used herein, may be permanent or may be bioerodable (used interchangeably with resorbable, or biodegradable herein), it may be charged or uncharged, may be a polymer or copolymer and can be a homopolymer or a blend/mixture.

In another embodiment, the medical device of the present invention comprises a biocompatible coating that further comprises a second polymer layer. The second polymer layer comprises a polymer and an NO generator. The polymers used for the first and second polymer layers can be the same or different in composition, construction, thickness and location. Moreover, the type and amount of NO generator used in each layer may be the same or different. In one particular embodiment, the first and second polymers are oppositely charged. Additional oppositely charged layers may be used as illustrated in FIG. 1(B).

In particular embodiments, the NO generator in the pyrolytic carbon is copper or a copper oxide. In particular embodiments, the medical device is a heart valve prosthesis, collapsible heart valve, annuloplasty ring, heart valve stent, heart valve leaflet, vascular stent, mechanical heart component, pacemaker component, electrical lead, or an orthopedic component such as an artificial joint, screw or plate and the NO generator is copper or a copper oxide.

In further embodiments, the biocompatible coating of the medical device of the instant invention comprises pyrolytic carbon and an NO generator, and further comprises one or more additional materials which improve strength, performance, flexibility, life, wear, and biocompatibility of the device. These additional materials may include, without limitation, polymers, pharmaceuticals or other biologically active materials (e.g., an antibacterial agent, antifungal agent, anti-rejection agent, anti-inflammatory agents, analgesics, pain medications, kinases), pH adjusting substances, a metal, metalloid, or metalloid carbide. Depending upon the additive, these may be part of the pyrolytic carbon coating layer or one or more polymer layers. In a particular embodiment, the carbide is silicon carbide.

In another aspect, the invention relates to methods of manufacturing a medical device comprising applying a biocompatible coating comprising pyrolytic carbon and at least one NO generator onto at least a portion of a surface of a substrate. In some embodiments, the biocompatible coating is applied by electrochemical deposition, super critical fluid deposition, chemical vapor deposition (CVD), physical deposition, chemical reduction, casting, dipping, layering, spray coating in a fluidized bed or otherwise, and combinations thereof. In further embodiments, ion-beam-assisted deposition or sputtering are used.

In another aspect, the present invention relates to a method of increasing the biocompatibility of a medical device comprising providing a biocompatible coating on a substrate to form a medical device. The biocompatible coating comprises pyrolytic carbon and at least one NO generator. In a particular embodiment, increasing the biocompatibility of the medical device comprises increasing the hemocompatibility of the medical device. In another embodiment, the present invention comprises a method of treating a mammalian patient in need of treatment by implanting into that patient a medical device comprising a substrate and a biocompatible coating comprising pyrolytic carbon and an NO generator.

In another aspect, the invention relates to a biocompatible composition comprising pyrolytic carbon and at least one NO generator.

In yet another aspect, the invention relates to the use of the medical device of the present invention to reduce the incidence of thromboses associated with the surgical implantation of a medical device in a patient in need thereof.

It is contemplated herein that the incorporation of NO generators and pyrolytic carbon according to the present invention will, in certain instances, contribute to an increase in biocompatibility of a medical device. Without wishing to be bound by any particular theory of operation, this increase in biocompatibility may be caused by an increase in hemocompatibility of the medical device for a period of time after surgical implantation in a patient. The increase in biocompatibility is believed due to an increase in NO in vivo, and a resulting NO-mediated reduction in the formation of blood clots, or thrombi, and/or by facilitating endothelialization of the medical device. The use of medical devices of the present invention may counteract an initial period of increased risk of thrombosis associated with the implantation of a medical device in a patient, as well as for a time beyond this initial period, via the natural anti-clotting function of NO. Additionally, the devices of the present invention may function to help recruit endothelial cells, and therefore promote endothelialization.

BRIEF DESCRIPTION OF THE DRAWINGS

FIG. 1 depicts a biocompatible coating comprising pyrolytic carbon and at least one NO generator in a layer on a medical device such as might be achieved by chemical vapor deposition of pyrolytic carbon and at least one NO generator (depicted as dots). Structure(B) of FIG. 1 depicts a medical device of the present invention wherein the biocompatible coating further comprises first and second polymer layers comprising an NO generator, and wherein the first and second polymers are oppositely charged (depicted as circles with either positive or negative charge within). Structure (C) depicts a medical device of the present invention wherein the biocompatible coating comprises at least one layer comprising pyrolytic carbon, and a first polymer layer comprising both at least one biodegradable polymer and at least one NO generator (depicted as dots).

DETAILED DESCRIPTION

Figure 1:
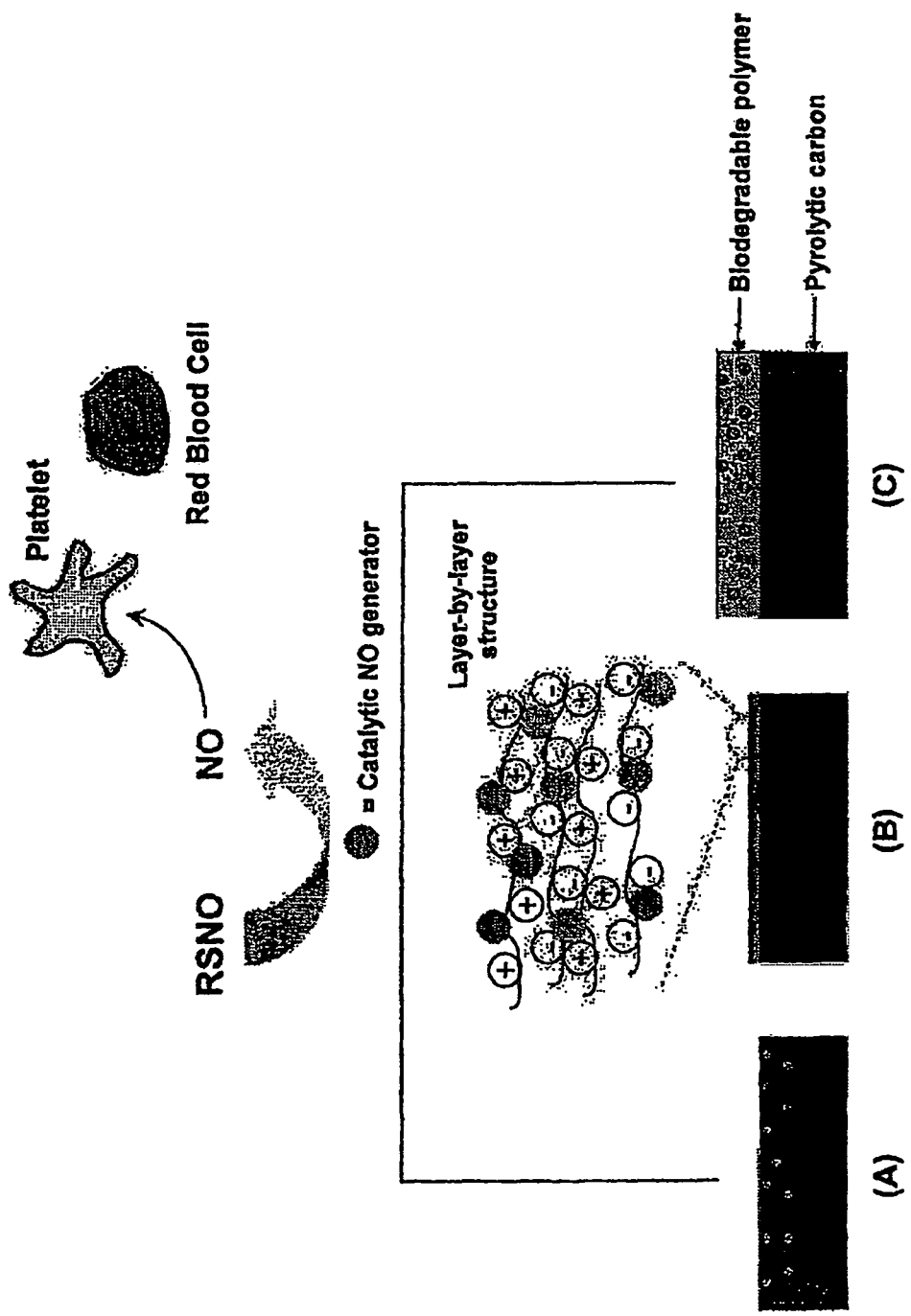
FIG. 1 depicts non-limiting examples of various ways in which NO generators can be incorporated into or onto the pyrolytic carbon surface of a medical device. NO=nitric oxide; RSNO=endogenous NO precursor nitrosothial species. Specifically, structure (A) within

While the specification concludes with the claims particularly pointing and distinctly claiming the invention, it is believed that the present invention will be better understood from the following description.

All percentages and ratios used herein are by weight of the total composition unless otherwise indicated herein; for example, the amount of NO generators present in a biocompatible coating of the present invention may be quantified as a percentage of total surface area of the substrate to which the biocompatible coating is applied. Alternatively, the quantity of NO generators may be determined as an atomic percentage. All measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "an NO generator" can mean at least one NO generator, as well as a plurality of NO generators, i.e., more than one NO generator.

A "medical device" as that term is used herein is meant to refer to any devices which are suitable for insertion or implantation in a patient and include both pyrolytic carbon and an NO generator. Most often, these devices are intended to be left with a patient (human or animal) for an extended period which can be as short as hours and as long as years following the procedure in which they were introduced. Medical devices include, without limitation, prostheses such as pacemakers, pacemaker components, electrical leads such as pacing leads, defibrillators, mechanical hearts, mechanical heart components, ventricular assist devices, including left ventricular assist devices, anatomical reconstruction prostheses such as breast implants, heart valve prostheses, including collapsible or non-collapsible heart valves, heart valve stents, heart valve leaflets, pericardial patches, surgical patches, coronary stents, vascular grafts, vascular and structural stents, vascular or cardiovascular shunts, biological conduits, pledgets, sutures, annuloplasty rings, stents, staples, valved grafts, dermal grafts for wound healing, orthopedic components, including orthopedic spinal implants, orthopedic pins, screws or plates, artificial joints, intrauterine devices (IUDs), urinary stents, maxial facial reconstruction plating, dental implants, intraocular lenses, clips, sternal wires, and combinations thereof. Additional devices include, without limitation, cannulas, drainage tubes such as chest tubes, or any other medical device in which an increase in biocompatibility is desirable.

As used herein, a "substrate" of a medical device of the instant invention refers to the native device. A native device is a pyrolytic carbon-containing device before an NO generator is added or a device which is not made of pyrolytic carbon before a biocompatible coating is applied.

As contemplated herein, both the medical devices and the substrates of the present invention may be manufactured according to conventional methods, and out of materials of proven suitability for such medical prostheses. For example, suitable materials for use as substrates will have desirable mechanical properties, such as elasticity or stiffness, strength, fatigue resistance, wear resistance and fracture toughness, without introducing excessive weight or bulk. These include, for example, metals, composites and/or alloys that provide the requisite structural strength and flexibility necessary for the particular function of the medical device. Suitable substances include, for example, pyrolytic carbon, pyrolytic carbon/carbide composites, metals, carbonaceous solids and ceramics. These materials may be coated with one or more compounds either during or after manufacture, e.g., with a polymer, protein, metal, metalloid, or other compound, prior to use, if desired. Suitable inert metals that may be used to manufacture the medical devices of the present invention include, for example, titanium, cobalt, stainless steel, nickel, iron alloys, cobalt alloys, such as ELGILOY, a cobalt-chromium-nickel-molybdenum-iron alloy, and MP35N, a nickel-cobalt-chromium-molybdenum alloy, and NITINOL, a nickel-titanium alloy. See, for example, U.S. Pat. No. 7,632, 309 and U.S. Pat. No. 7,604,663 the entire contents of which are incorporated by reference herein.

The biocompatible coatings of the invention include pyrolytic carbon and an NO generator. As used herein, the term "biocompatible" refers to materials that are non-toxic and meets ISO standards for medical devices, e.g., ISO-10993, "Biological Evaluation of Medical Devices", and particularly, Part IV regarding selection of tests for interaction with blood.

The biocompatible coatings may further comprise one or more additional materials which improve strength, performance, flexibility, life, wear, and biocompatibility. The selection of additional materials depends on a number of factors, including their function and their intended location. For example, a pharmaceutical agent would not likely be included as part of a pyrolytic carbon layer due to the temperature at which the layer is formed. It might, however, be part of a polymer layer forming part of a biocompatible coating. Additional materials may include, without limitation, polymers, pharmaceuticals or other biologically active materials (e.g., an antibacterial agent, antifungal agent, anti-rejection agent, anti-inflammatory agents, analgesics, pain medications, kinases), pH adjusting substances, metal or metalloid carbide. In a particular embodiment, the metalloid carbide is silicon carbide, added to enhance the mechanical property of the pyrolytic carbon.

As used herein, pyrolytic carbon refers to a material similar to graphite but with some covalent bonding between its graphene sheets. It can be produced by heating a hydrocarbon nearly to its decomposition temperature and permitting the graphite to crystallize. Pyrolytic carbon can exist in a wide range of microstructures and varied content of residual hydrogen. Pyrolytic carbon as used herein includes pyrolytic carbon alone, or in combination with other substances, e.g., to improve the biocompatibility as well as the mechanical and structural capabilities of the coating. For example, U.S. Pat. No. 7,632,309 describes the use of pyrolytic carbon in combination with a metal or metalloid. A "metalloid", also known as a "semi-metal", refers to an element which has properties between that of a metal and a nonmetal. Examples of metalloids include, e.g., elements such as silicon and selenium.

Generally, in the manufacture of a medical device in accordance with the invention, pyrolytic carbon is deposited on the substrate by the pyrolysis of a hydrocarbon gas, typically in a temperature range from about 1000° C. to about 2500° C. With propane as the hydrocarbon source, the typical temperature range is from about 1100° C. to about 1800° C. The temperature range can be varied according to precursors used. At least some carbides can be conveniently deposited by comparable pyrolysis. Thus, introduction of the appropriate blend of precursor compounds into the pyrolytic reactor can result in the production of pyrolytic carbon, carbide compound or mixtures thereof.

If the precursors of pyrolytic carbon and the metal/metalloid carbide are blended in the reaction vapor, an "alloy" or mixture of the pyrolytic carbon and carbide materials is formed where the two materials are mixed in the sense that grains or crystallites of each material form domains or phases adjacent to domains or phases of the other material. The deposition methods include, without limitation, chemical vapor deposition, plasma assisted chemical vapor deposition and fluidized bed chemical vapor deposition. In particular, chemical vapor deposition can be performed in a fluidized reactor. Liquid phase chemical vapor deposition is also possible. Liquid phase vapor deposition is described generally in "Liquid fluidized bed coating process," by Lackey in the journal, *Carbon* 34 (10):1299-1300 (1996). Fluidized bed chemical vapor deposition is a typical method. The temperature and/or other reactor variables, such as vapor flow rates, can be varied during the deposition of the composite depending on the composition being deposited at a particular point in time.

Suitable pyrolytic carbon precursors include, for example, hydrocarbon gases, such as methane, ethane, propane, ethylene, acetylene, and mixtures thereof. Suitable silicon carbide pyrolysis precursors include, for example, methyl silane and methyl trichlorosilane. Metal carbide precursors can include metal halogens, such as metal chlorides, in which the metal is the desired metal for the corresponding metal carbide. The hydrocarbon gas or an inert gas, such as argon, nitrogen, helium, or mixtures thereof, can be bubbled through a liquid carbide precursor to serve as a carrier gas that assists with the delivery of desired amounts of the vapor of the precursor compound. A nitrogen containing compound can be included for the deposition of a quantity of metal/metalloid nitride.

In one approach to a pyrolysis reaction, the reactant vapors are directed into a reaction furnace. The substrate is mounted in the reaction furnace. The furnace generally is kept at a wall temperature from about 1000° C. to about 2500° C. using any reasonable heating approach, such as induction, radiant or resistance heating. Generally, higher temperatures are used for the deposition of carbides than for the deposition of pyrolytic carbon. The particular preferred temperature will depend on the particular precursors, flow rate and reactor design. With some deposition approaches, the substrate can be rotated to obtain an even coating. Similarly, the substrate can be movable to provide desired variation in the coating thickness at different locations on the substrate depending on the orientation of the substrate with respect to reaction flow over the course of the entire coating process.

In a commonly used approach, the pyrolysis reaction/chemical vapor deposition is performed in a fluidized bed reactor. In particular, the substrate is placed within a bed of particles, such as zirconia beads, that are fluidized by the flow of reactant and carrier gases. Pyrolytic carbon can be deposited within a fluidized bed reactor using hydrocarbon gases as reactants. The fluidized bed reactor preferably is set at a temperature selected in part upon the particular reactant gases and is typically at a temperature from about 1000° C. to about 2500° C. and more typically from about 1100° C. to about 1800° C. Alternatively, the reaction can be performed in a liquid-phase chemical vapor deposition reactor. In this liquid-phase process, the reagents are liquids that are fluidized by the flow of inert gases. A liquid fluidized bed deposition process is described further in Lackey et al., "Liquid Fluidized Bed Coating Process," *Carbon* 34 (10):1299-1300 (1996).

The medical devices and biocompatible coatings of the invention also include an NO generator. As used herein, an "NO generator" (also referred to interchangeably herein as a "catalyst" or "NO catalyst"), refers to any compound that may safely cause the formation of NO in a patient surgically implanted with a medical device according to the present invention. Such compounds may be inorganic or organic. Organic compounds include copper, selenium or another desirable metal. Such compounds are more traditionally known as organometallic compounds. During the formation of the pyrolytic carbon layer, these organometallic compounds may be added to the reactor or the fluidized bed. Because of the heat involved, the organic materials combust leaving the metal, generally in a very fine particle to be distributed as part of the coating. It is difficult to accurately describe the particle size of these metallic species prior to coating creation. It is also difficult to provide an average particle size once they are part of the coating. However, from SEM or similar imaging techniques, the particle sizes are expected to range from about 0.1 nm up to approximately about one micron. Indeed, it is expected that the particle sizes will tend to be on the smaller side of this range. An example of an organometallic material useful in the present invention is copper acetate. This may include, for example, copper (II) acetate or copper (I) acetate. Useful copper based species may also include, e.g., copper(II) naphthenate, copper(I) methylsalicylate, copper(II) 2-ethylhexanoate, copper(II) 3,5-diisopropylsalicylate, copper(II) acetylacetonate, copper(II) cyclohexanebutyrate, copper(II) D-gluconate, and copper(II) formate.

Inorganic materials are generally metals themselves or metal based species such as an oxide. Copper and copper II oxide are examples.

Chalcogenide compounds are known NO generators. A "chalcogenide compound" or "chalcogen," as used interchangeably herein, refer to compounds and moieties that include atoms within column 6A of the periodic table. Group 6A or chalcogen compounds may also be referred to as Group 16 compounds. Group 6A atoms include oxygen, sulfur, selenium, tellurium, and polonium. Common to all of the NO generators is the ability to cause the conversion of nitrosothials, a naturally occurring NO source, into physiological levels of NO which can act in vivo as an anti-clotting factor. Generation of NO in vivo in this way can also help recruit endothelial cells to promote endothelialization of the surface of the medical device.

The biocompatible layer(s) and coatings comprising pyrolytic carbon and an NO generator contemplated herein can be formed by processes familiar to those of skill in the art. In one embodiment, the surface of a substrate which includes pyrolytic carbon can have an NO generator coated over or incorporated into a portion of its surface. In still another embodiment, the pyrolytic carbon in combination with the NO generator may be applied to a substrate. This may be accomplished, for example, by chemical vapor deposition ("CVD") and/or physical deposition, or variants of chemical vapor deposition including, but not limited to, plasma enhanced or plasma assisted chemical vapor deposition.

For example, an NO generator such as Cu or Se or their oxides can be added to a substrate that already includes pyrolytic carbon or has been coated with pyrolytic carbon. These NO generators may also be coated onto a substrate along with pyrolytic carbon. FIG. 1(A) illustrates the deposition of pyrolytic carbon and an NO generator to create a biocompatible layer. There are several aspects of this FIGURE which are noteworthy. First, the circles or dots representing the NO generator are not distributed completely throughout the layer, but are aggregated near one surface as illustrated. This may occur by first coating a substrate with a layer of pyrolytic carbon and thereafter placing an additional coat over the top of the initial coat. This second coat includes both pyrolytic carbon and an NO generator. Alternatively, in one particular embodiment this can be accomplished by a chemical vapor deposition process where both an organometallic compound and a pyrolytic carbon precursor are used. The relative proportion of the NO generator to pyrolytic carbon can be varied and controlled by, for example, the feed rate or amount of each material. A structure as illustrated in FIG. 1(A) could result from an initial CVD process in which only a pyrolytic carbon precursor, such as propane, is fed into the reaction chamber. Thereafter, an NO generator can be introduced as well to create a biocompatible layer.

Alternatively, the NO generator can be added physically. For example, relatively large particles of zirconium oxide (ZrO) are used with relatively smaller particles of copper to bombard a vapor deposited layer of pyrolytic carbon. This can occur while the carbon layer is building up and/or thereafter. Copper particles can also be added to the reaction chamber and applied while the pyrolytic carbon coating is being built up. This is another form of physical deposition. In either of these physical deposition processes, the size of the NO generator particles will tend to be larger and less evenly dispersed than would result from CVD using an organometallic material. Average particle size, determined using a scanning electron microscope (SEM) or other similar imaging technique semi-quantitatively will yield a particle size range of from about 1.0 nm to about 100 microns. Particle size ranges and averages can be determined more accurately for these particles prior to deposition but particle size or distribution in the biocompatible coating may vary.

The amount of NO generator particles can depend on a number of factors. The type of device, the manner in which the NO generator is applied, and the material used for the NO generator are all factors. Sufficient NO generator particles are necessary to provide a meaningful improvement in the biocompatibility. However, too high an NO generator content could raise toxicity issues or could compromise the physical properties of the pyrolytic carbon. NO generator particles located beneath the pyrolytic carbon surface may play a limited role, if any, in increasing the biocompatibility of the device. Therefore, the NO generator should comprise relative to the total surface area of the biocompatible coating greater than 0%, typically at least about 0.05%, and comprise no more than about 5%, of the total surface area as measured by, for example, X-ray photon spectroscopy (XPS). In another embodiment, it comprises no more than about 3%, and in a still further embodiment, it comprises from about 0.05% to about 3%. For example, with larger devices, a survey area of about 4 mm$^2$ can be used. For smaller devices, a much smaller area could be used. The survey area will vary with the device, technique and the size of the device.

The biocompatible coating can range in thickness from about 0.01 to about 2000 microns. In some embodiments, the thickness will range from about 0.05 to about 500 microns and in still another embodiment from about 0.1 to about 100 microns. This is measured at any single point on the coated medical device. Of course, since the NO generator material most important to the biocompatibility is located at the surface, one may create a coating having an overall thickness of up to about 2 millimeters where only the upper portion is a biocompatible coating, i.e., contains both pyrolytic carbon and an NO generator. For example, an artificial heart valve, especially the orifice part, can be coated with a 900 micron thick layer of pyrolytic carbon and thereafter coated with a 100 micron thick layer of pyrolytic carbon and NO generator to yield an overall coating thickness of about 1 millimeter. As the leaflet part of a heart valve is typically thinner (approximately 1 millimeter), the coating on this part may be, e.g., approximately 100 microns.

In addition to a medical device wherein the biocompatible coating comprises at least one layer which comprises the pyrolytic carbon in combination with the NO generator, it is also contemplated herein that NO generators such as, for example, copper and/or selenium-based NO generators, can be introduced on top of a pyrolytic carbon layer. This can be done in several ways including mixing the NO generator with a polymer and forming one or more layers over the surface of the pyrolytic carbon. In one embodiment, this is accomplished by using a layer-by-layer (LBL) technique (Yang et al., *Langmuir* 2008, 24, 10265-10272). Unlike the previously described embodiment, this approach is performed after the pyrolytic carbon coating process is completed on a medical device, e.g., after deposition of pyrolytic carbon on a leaflet or orifice substrate via, for example, CVD. The contemplated biocompatible coating may be applied to cover the entire surface of the medical device, or just a portion thereof, for example, as a discrete patch applied to a specific location on the surface of the device, or to a particular component of the device, e.g., to an orifice or leaflet, of a mechanical heart valve. Catalytic activity could be localized to a particular site in vivo in this manner. In like manner, a biocompatible coating could be placed on one portion of a metal or graphite device, and not other portions. For example, it could be placed on an area of a collapsible stent that itself does not collapse.

Thus, as envisioned herein, a medical device of the present invention may comprise a biocompatible coating which comprises at least one layer comprising pyrolytic carbon, a first layer comprising at least one polymer and at least one NO generator, and, in some embodiments, a second or subsequent polymer layer(s) comprising an NO generator. In one particular embodiment illustrated in FIG. 1(B), the first and second polymers are oppositely charged.

A medical device with an "LBL coating" of the present invention may be created, for example, by utilizing static interactions between positively charged species and negatively charged polymer species to build multiple layers of species of interest onto a charged surface. For example, as a first step to form robust LBL on post-CVD pyrolytic carbon valve components, the carbon materials should be chemically or physically treated to introduce surface charges. This can be achieved, for example, by soaking the pyrolytic carbon in various chemical solutions familiar to one of skill in the art to generate different surface functional groups, or physically treating the pyrolytic carbon surface with plasma, and thereafter introducing either a positive or negative charged surface via pH adjustment. For example, treating the carbon surface with a concentrated sodium hydroxide solution may introduce hydroxyl (—OH) groups onto the outmost surface of a silicon alloyed pyrolytic carbon via Si—OH and/or C—OH functional groups. After washing steps, the functionalized surface can be further buffered in a basic solution to generate a negatively charged surface with metal counter ions.

Thereafter, a positively charged layer (e.g., a water-soluble, positively charged polymer, for example polyethyleneimine (PEI) or polylysine—in solution A) can be put down on the surface via static interaction as the first polymer layer. This can be achieved by quickly dipping the substrate into the aqueous polymer solution, followed by washing steps. The substrate can then be dipped into a negatively charged polymer solution, for example, heparin, alginate or poly(4-styrenesulfonic acid) (PSS) (solution B). The cycle (solution A—washing—solution B) can be repeated until a desired number of layers or thickness is achieved. Both positively and negatively charged polymers can be water-soluble synthetic or natural polymer species bearing NO generators. For example, the NO generators can be a Cu- and/or Se-based complex that are either incorporated into the LBL structures by static interactions or by covalent bonding. As understood by one of skill in the art, the NO flux (i.e., the increase in NO) generated from the LBL-coated pyrolytic carbon can be controlled by the species and concentration of the NO generators within the polymer, by the number of layers, by the polymer properties, etc. In addition, it is also understood herein that the thickness of the LBL coating depends on the number of cycles of alternating layers that are deposited.

In another embodiment, a medical device of the present invention may comprise a biocompatible coating which comprises at least one layer comprising pyrolytic carbon, and a first layer comprising at least one polymer and an NO generator, wherein the polymer used is biodegradable. This is illustrated in FIG. 1(C). Thus, for example, one or more biodegradable polymer coatings or layers can be applied to a medical device following the CVD pyrolytic carbon coating process of the device, e.g, heart valve components. NO generators (e.g., Cu- and/or Se-based complex) are incorporated into this biodegradable polymer coating.

As understood herein, when a biodegradable polymer is used in the biocompatible coating of a medical device of the present invention, a short-term, or limited, supply of NO may be generated in vivo because once the polymer is fully degraded, NO generation from the surface will cease. Even a short term increase in NO generation in vivo is beneficial, however, since such catalytic NO generation from the implant surface advantageously reduces clotting risk during the initial post-implant period. In addition, NO generation in this way can promote the prohealing process of endothelialization (if the surface properties and/or morphology are appropriately modified to attract ECs). It is understood herein, that once endothelialization of the medical device is completed, the device, e.g., an artificial valve, can rely on the restored natural function of the endothelial cells to prevent clotting. As such, the need for additional assistance from biomimetic NO generation is minimal, or ideally, not necessary.

As described above, a "biodegradable polymer" is one which may comprise an NO generator and which may erode or be resorbed in vivo. As understood by one of skill in the art, the selection of a biodegradable polymer for use in the methods of the present invention may depend on various factors. For example, the selection of polymer will depend on the time required for completion of the initial endothelialization on the surface of the medical device (e.g., valve) during the prohealing process. The known degradation period for various polymers may vary widely and range, e.g, from a couple of months to a couple of years. In addition, the hydrophobicity and compatibility of the polymer with the incorporated NO generators and/or other endothelialization factors (as well as the amount of those other factors) are considerations that can affect performance.

Polymers for use in medical devices and biocompatible coatings are familiar to one of skill in the art. These include, for example, biocompatible polymer materials which can be fabricated from synthetic polymers as well as purified biological polymers. These synthetic polymeric materials can be formed into fibers and/or yarn and then woven or knitted into a mesh to form a matrix or similar structure. Alternatively, the synthetic polymer materials can be molded, extruded, dip coated or cast into appropriate forms.

Appropriate synthetic polymers for use in medical devices include, for example, polyamides (e.g., nylon), polyesters, polystyrenes, polyacrylates, vinyl polymers (e.g., polyethylene, polytetrafluoroethylene, polypropylene and polyvinylchloride), polycarbonates, polyurethanes, poly dimethyl siloxanes, cellulose acetates, polymethyl methacrylates, ethylene vinyl acetates, polysulfones, polyacetals, nitrocelluloses and similar copolymers.

Other suitable polymers include biodegradable (also referred to herein as "resorbable", "erodable" or "bioerodable") polymers such as dextran, hydroethyl starch, derivatives of gelatin, polyvinylpyrrolidone, polyvinylalcohol, poly[N-(2-hydroxylpropyl) methacrylamide], polyglycols, polyesters, poly(orthoesters), poly(ester amides), and polyanhydrides. Biodegradable polyesters include, for example, poly(hydroxy acids) and copolymers thereof, poly(caprolactone), poly(dimethyl glycolic acid), and poly(hydroxy butyrate). Biodegradable polymers are contemplated for use in the present invention, for example, in a medical device comprising a biocompatible coating comprising at least one layer comprising pyrolytic carbon, and a first layer comprising at least one biodegradable polymer and an NO generator. Typical biodegradable polymers for use with the present invention include, for example, D, L-polylactic acid, L-polylactic acid (PLA), poly(glycolic acid) (PGA), and copolymers of L-lactic acid, D-lactic acid and glycolic acid such as poly(lactic-co-glycolic acid) (PLGA). These are all, of course, non-limiting examples. Any other polymer material (including copolymers, homopolymers and polymer mixtures) which can accomplish the goals of the embodiments of the invention are contemplated.

One of skill in the art will understand that polymers for use in the biocompatible coatings may include various properties, but as contemplated herein, all must function in the biocompatible coating of a medical device of the present invention without negatively impacting the mechanical or structural features required for successful operation of the medical device in vivo. For example, a medical device comprising a biocompatible coating comprising at least one layer which comprises the pyrolytic carbon in combination with the NO generator may further include a polymer, which will typically be a nonresorbable biocompatible polymer which does not negatively impact the function of pyrolytic carbon, or otherwise disturb the mechanical or structural properties of the medical device.

Similarly, polymers may also be used as described herein as first and second layers comprising NO generators, and particularly, in a layered arrangement of oppositely charged polymers comprising NO generators applied to a layer of pyrolytic carbon. Charged polymers particularly suitable for these purposes include, for example, polyethyleneimine (PEI) or polylysine, heparin, alginate or poly(4-styrenesulfonic acid) (PSS).

As discussed herein, pyrolytic carbon may be deposited onto a substrate material in combination with a metal, metalloid or other materials. As contemplated herein, certain NO generators may be deposited with pyrolytic carbon in a manner similar to that by which silicon is doped during CVD into the pyrolytic carbon coating of a medical device to form silicon carbide (SiC) as described in U.S. Pat. No. 7,632,309 cited above. From about 5 to 12%, typically about 10% silicon, may be doped during this process, however, it is understood herein that the amount of material to be added such as, for example, gaseous silicon or an organometallic NO generator, will be varied to provide the desired level of carbide or NO generator in the biocompatible layer.

For example, during the pyrolysis step in the manufacture of a pyrolytic carbon-coated device, a small amount of copper or organic copper complex particles such as copper acetate (e.g., micron to nano scale) can be introduced into a reactor with the reaction gas stream. In one embodiment, the reaction gas stream may comprise propane ($C_3H_8$), methyltrichlorosilane ($CH_3Cl_3Si$), and helium. As contemplated herein, the gas stream fluidizes (i.e., supports and agitates) a bed of granular materials in which the components to be coated (for example, leaflets or orifices) are suspended. The fluidized bed, which is heated by a furnace, in turn heats the gases and particle mixture as they pass up through the bed. When sufficiently hot, the gases decompose to form solid products (e.g., carbon, copper and silicon carbide) which deposit as a coating onto the leaflet and orifice substrates where tiny copper particles are codeposited on the surface or embedded in the silicon-alloyed pyrolytic carbon coating.

The SiC present in silicon-alloyed pyrolytic carbon does not dissolve in the carbon matrix, and the copper particles will also be present as discrete-phase particles, similar to the way that crystalline silicon carbide does (the size of SiC grains typically varies from about 1-1000 nm, with about 8 nm being typical).

In addition to the co-deposition of silicon carbide, described previously, other suitable carbides for "alloying" with pyrolytic carbon and/or NO generators include, for example, boron carbide, tungsten carbide, tantalum carbide, niobium carbide, vanadium carbide, molybdenum carbide, aluminum carbide, zirconium carbide, titanium carbide, hafnium carbide (HfC) and mixtures thereof. As contemplated herein, the pyrolytic carbon-carbide "alloy" is deposited as a mixture where the metal/metalloid carbide and the pyrolytic carbon reside in distinct domains or phases. Generally, materials deposited on the substrate may comprise greater than about 50% by volume pyrolytic carbon, preferably at least about 75% by volume pyrolytic carbon, more preferably at least about 80% by volume pyrolytic carbon, and even more preferably at least about 90% by volume pyrolytic carbon.

In addition to the technique describe above, it is also contemplated herein that the carbide particles may serve as a vehicle for deposition of the NO generator. For example, zirconium oxide particles can be immersed in a copper organic complex solution (e.g., 5% copper acetate aqueous solution) and dried (e.g., at 100° C. overnight), to produce a thin layer of organic copper complex that is evenly coated on the zirconium oxide particles. After being introduced to the reaction chamber together with the reaction gas stream, the organic copper complex will be vaporized and decomposed at high temperature in the chamber. The resulting tiny particles of copper or copper oxide coming off the zirconium oxide particles are expected to deposit onto the substrate (e.g., on leaflet and orifice substrates of a heart valve) together with the silicon-pyrolytic carbon "alloy" in a uniform manner. As understood by one of skill in the art, the copper loading can be controlled by controlling the coating thickness on the zirconium oxide particles.

Thus, as described in detail herein, the current invention employs a biomimetic approach to enhance the biocompatibility, e.g., the hemocompatibility, medical devices via the use of pyrolytic carbon and NO generation. Without being limited to any particular mechanism of action, it is believed that when in contact with patient blood flow, a pyrolytic carbon based medical device comprising NO generators will locally generate a low level of NO at the blood/pyrolytic-carbon interface to prevent platelet adhesion, thereby preventing clotting. The level of NO that may be generated in vivo can be fine-tuned in various ways familiar to one of skill in the art to generate levels of NO that mimic that which is produced by endothelial cells in vivo. As understood herein, such NO levels are non-toxic, and designed to reduce the need for the use of anti-coagulants in a patient after surgical implantation of a medical device of the present invention in the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A medical device, comprising:
a substrate having a surface; and
a biocompatible coating in contact with at least a portion of the surface of the substrate, the biocompatible coating comprising pyrolytic carbon, at least one NO generator, and a biodegradable polymer, wherein said biocompatible coating is a single layer comprising pyrolytic carbon in combination with a NO generator, wherein an in vivo increase in NO by said NO generator promotes endothelialization of said device, and wherein said biodegradable polymer is selected from the group consisting of poly(lactic-co-glycolic acid), polyglycolic acid, polylactic acid, and polycaprolactone.

2. The medical device of claim 1, wherein the substrate is selected from the group consisting of graphite, metal and ceramic.

3. The medical device of claim 1, wherein the NO generator comprises no more than about 5% of the total surface area of the biocompatible coating.

4. The medical device of claim 1, wherein the biocompatible coating has a thickness of from about 0.01 to about 2000 microns.

5. The medical device of claim 1, wherein the NO generator is selected from the group consisting of chalcogens, copper, or oxides thereof.

6. The medical device of claim 5, wherein the NO generator is copper or copper oxide.

7. The medical device of claim 5, wherein the chalcogen is selenium.

8. The medical device of claim 1, wherein the medical device is selected from the group consisting of a heart valve prosthesis, an annuloplasty ring, a heart valve stent, a heart valve leaflet, a vascular stent, a urinary stent, a mechanical heart component, a pacemaker component, an electrical lead, a left ventricular assist device, and an orthopedic component.

9. The medical device of claim 8, wherein the heart valve prosthesis is a noncollapsible heart valve prosthesis.

10. The medical device of claim 1, wherein the biocompatible coating further includes a metal or a metalloid carbide.

11. The medical device of claim 10, wherein the metalloid carbide is silicon carbide.

12. The medical device of claim 1, wherein the biocompatible coating includes a plurality of NO generators.

13. The medical device of claim 1, wherein the biocompatible coating has a thickness of from about 0.05 to about 500 microns.

14. The medical device of claim 1, wherein the biocompatible coating has a thickness of from about 0.1 to about 100 microns.

* * * * *